United States Patent

Dreiling, deceased et al.

[11] Patent Number: 5,139,512
[45] Date of Patent: Aug. 18, 1992

[54] SEMIAUTOMATIC COMPRESS

[76] Inventors: Leo D. Dreiling, deceased, late of Midway City; by Marilyn Dreiling, heiress, 8200 Bolsa #76, Midway City, both of Calif. 92655

[21] Appl. No.: 599,476

[22] Filed: Oct. 18, 1990

[51] Int. Cl.5 .............................................. A61B 17/12
[52] U.S. Cl. .................................. 606/201; 606/203; 606/217
[58] Field of Search ........................... 606/201–204, 606/217

[56] References Cited

U.S. PATENT DOCUMENTS

| | | | |
|---|---|---|---|
| 2,571,461 | 10/1951 | Livingston et al. | 606/201 |
| 2,959,171 | 11/1960 | Seligman | 606/201 |
| 3,050,064 | 8/1962 | Moore et al. | 606/201 |
| 4,036,229 | 7/1977 | Marinello | 604/289 |
| 4,243,039 | 1/1981 | Aginsky | 606/203 |
| 4,742,825 | 5/1988 | Freund et al. | 606/158 |

Primary Examiner—Mickey Yu
Assistant Examiner—Kerry Owens

[57] ABSTRACT

The present invention is a semiautomatic compress which performs the function previously performed by a nurse exerting 30 pounds of pressure with her hand on a patient after insertion of a tube into a patient's artery, followed by compression by a sand bag for about ten hours. The compress comprises belts coupling it to the patient, and a calibrated ratchet controlled clamp which exerts a selected force on the wound of the patient for about ten hours while the blood of the patient clots at and near the wound.

2 Claims, 2 Drawing Sheets

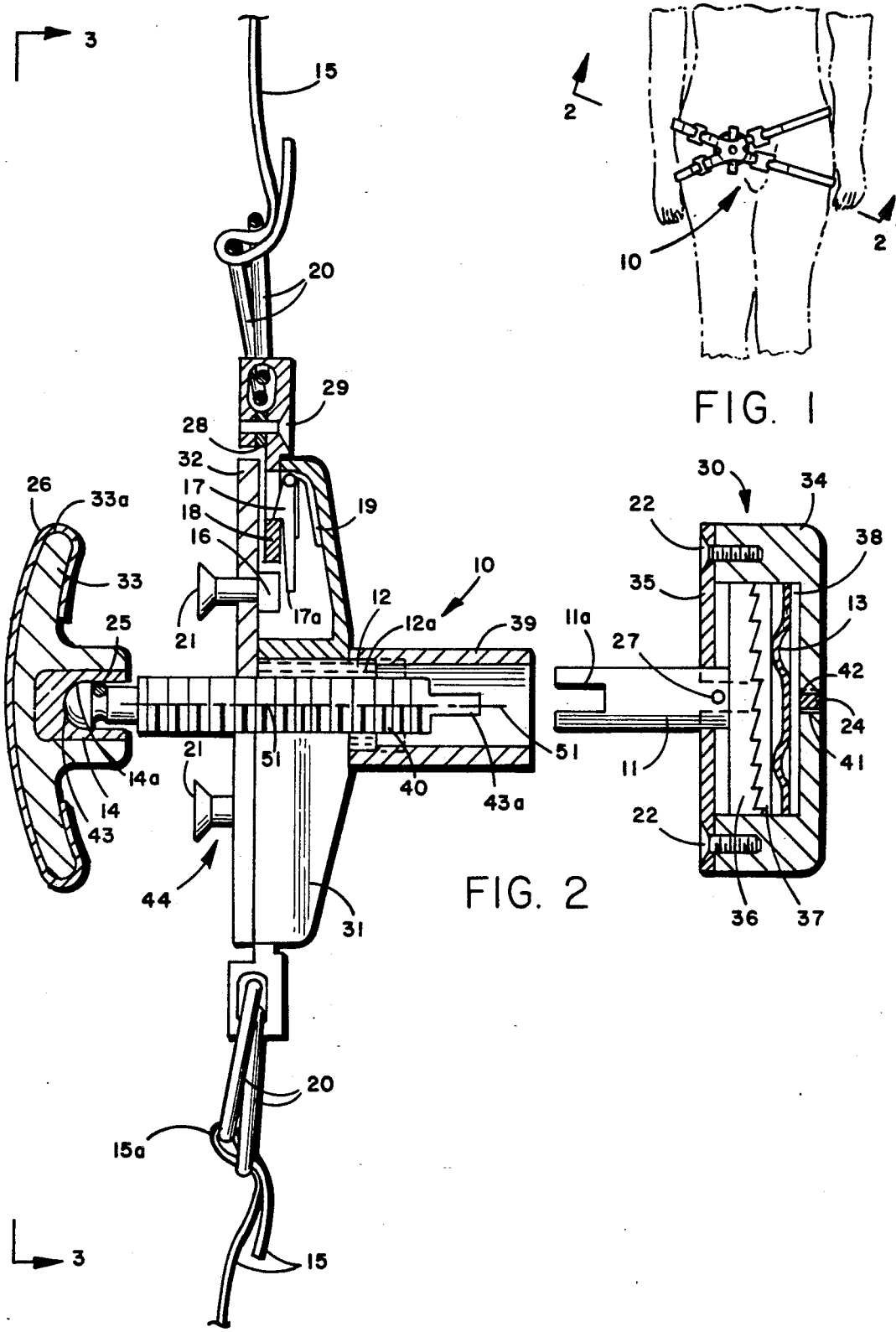

SEMIAUTOMATIC COMPRESS

BACKGROUND OF THE INVENTION

1. Field of the Invention

The present invention relates to semiautomatic compresses useful in preventing blood flow out of a wound caused by an invasive procedure into an artery or the like for a sufficient time to permit clotting.

2. Description of the Prior Art

Modern medicine combines miniaturization of certain instruments with greater knowledge to permit new invasive techniques into arteries, such as arteriograms and angiograms.

In this technique, a surgical incision opens an artery in a selected area such as the groin, and a selected instrument such as a television camera coupled to a lens via fiber optics is utilized to view a selected part of the interior of a human body. The lens, coupled to fiber optic wire or cable is inserted through an artery, usually through a tube inserted for the purpose. A light may be utilized so that the lens receives back sufficient radiation for the desired purpose. The preceding two paragraphs describe prior art techniques and knowledge not claimed in the present invention.

After an intervention as described previously herein, the patient is left with a wound which includes a hole through the outer skin, artery wall, and all the tissue in between. The artery is large enough and the blood pressure is great enough so that the patient would bleed to death unless appropriate measures were taken to stop the bleeding and begin healing of the wound.

In the prior art, these measures include hand pressure of about 30 pounds against the outer skin of the patient surrounding the wound for hours to ensure clotting. This is very uncomfortable for the patient who must remain in an unnatural position relatively motionless. This is difficult for the nurse who must exert a strong force, but not too strong a force which exertion tires her quickly, but nevertheless she must maintain the force. Sometimes bleeding resumes when fatigue forces the nurse to switch hands or when one nurse relieves another nurse or when the patient moves. Sometimes the resumed bleeding leads to complications which injure or kill the patient.

What is needed, but not disclosed by the prior art is a semiautomatic or automatic compress which would stop bleeding long enough for clotting without forcing the patient to remain in one unnatural position for a very long time during the clotting process and without exposing the patient to the risks of nurse or patient fatigue, cramping, or other very human problems which have caused bleeding to resume in many patients.

SUMMARY OF THE INVENTION

A semiautomatic compress is presented. A first example of the compress comprises:

adjustable belt means;

a base disposed around a center axis and including a clamping assembly coupled to compress means and release means;

coupling means coupling the belt means to the clamping assembly;

a torque adjustor coupled to the clamping assembly to adjust torque, the torque adjustor comprising ratcheting means causing the torque adjustor to ratchet when a selected torque is exceeded;

In said example, the base has four buckles disposed to define the corners of a rectangle at the four corners of the base, each buckle being removeably coupled to the base by a different one of four swiveling spring loaded base latches, each of two pairs of latches having an end which is released by one of a pair of latch release bars in turn controlled by a stripper bolt extending out of the base so that pushing in a stripper bolt pushes in a coupled latch release bar which pushes two latches, releasing two buckles, each latch spring pushing the latch against the coupled latch release bar and also against the coupled buckle, the interior surface of the base defining female threads which define an axial drive screw tunnel, having a male threaded drive screw coupled therethrough, the screw having an exterior rounded end having a dowell, the interior end of the screw defining torque assembly coupling means;

a clamping pad assembly having a sleeve defining an interior surface rotatably swivelingly coupled to the rounded end having a dowell of the drive screw and an exterior surface opposite the interior surface which exterior surface defines a clamping pad of selected size and shape, wherein the clamping pad is covered by a clamping pad cover of selected composition;

a clamping driver having one end surface shaped to removeably rotatably couple to the axial drive screw torque assembly coupling means, the clamping driver including means to adjust said driver to ratchet at a selected torque;

the adjustable belt means comprises two belts which would, if extended, intersect at a selected angle at the base and which do intersect at approximately their midpoint 180 degrees from the base, and the coupling means comprise D-rings coupling each belt end to a separate buckle on the base.

In a preferred example, the clamping driver includes a spring controlled ratcheting mechanism controlling a ratcheting gear which spring controlled ratcheting mechanism is controlled for selected torque by a set screw.

Prior to installation, the compress is calibrated by tightening or loosening the screw which compresses or loosens a torque spring which changes the pressure on the ratchet gear until the selected ratcheting torque is obtained.

The belts are then adjusted to fit the patient.

The selected procedure is then performed on the patient. After the angiogram, arteriogram or other procedure is completed, and just before the tube, other mechanism or catheter is removed from the body of the patient, the belt is placed around the patient with the clamp above the wound. The tube or catheter is removed while pressure is placed on the wound to stop or prevent bleeding. The clamp is then tightened down by rotating the spring controlled ratcheting mechanism. After a selected time which may be up to ten hours or more, the wound has stopped bleeding because of clotting and the compress is removed. The patient can move around during this time, a substantial improvement over the prior art where a nurse uses her hand to compress for perhaps 30 minutes, then the patient lies in only one position which usually becomes cramped and uncomfortable under a sandbag for about ten hours.

DRAWING DESCRIPTION

Reference should be made at this time to the following detailed description which should be read in conjunction with the following drawings, of which:

FIG. 1 illustrates a patient wearing a semiautomatic compress according to the present invention;

FIG. 2 illustrates a partially cutaway side view of the semiautomatic compress of FIG. 1 along the line 1—1.

DETAILED DESCRIPTION

Figure 3:
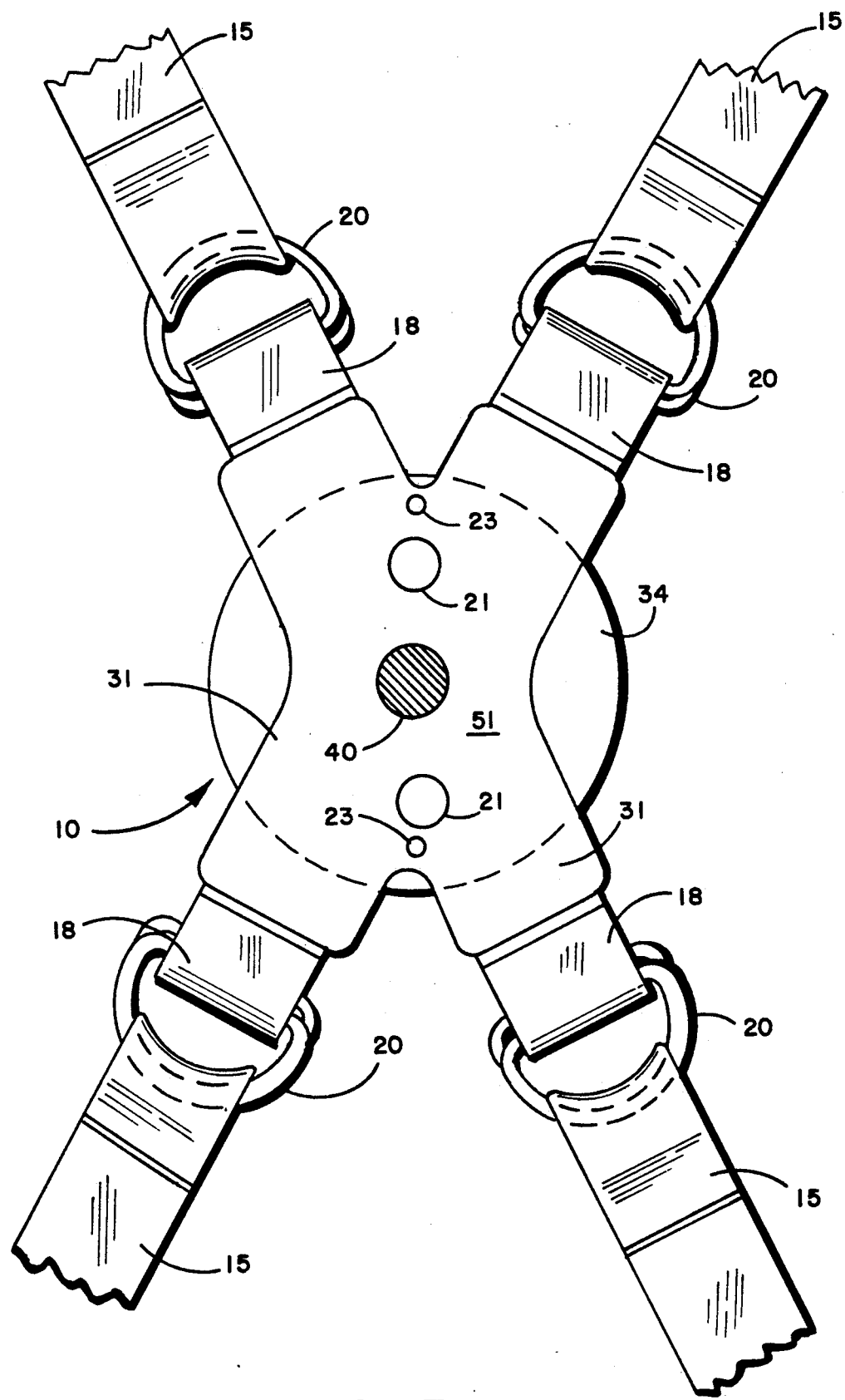
FIG. 3 illustrates a more detailed view of the semiautomatic compress of FIG. 2 along the line 3—3.

Reference should be made at this time to FIGS. 1-3 which illustrate various views of a semiautomatic compress 10 according to the present invention. A first example of the compress 10 comprises:

adjustable belt means 15;

a base 31 disposed around a center axis 51 and including a clamping assembly 44 coupled to compress means 33a comprising a clamp pad 33 and release means 21 also called two stripper bolts 21, each coupled to release a different one of a pair of buckles 18;

coupling means comprising four D rings, 20, each D ring 20 coupling a different one of four ends 15a of the belt means 15 to the clamping assembly 44;

a torque adjustor 30 coupled to the clamping assembly 44 to adjust torque, the torque adjustor 30 comprising ratcheting means 36, 37 causing the torque adjustor 30 to ratchet when a selected torque is exceeded;

In said example, the base 31 has four buckles 18 disposed to define the corners of a rectangle at the four corners of the base 31, each buckle 18 being removeably coupled to the base 31 by a different one of four swiveling spring loaded base latches 17, each of two pairs of latches having an end 17a which is held or latched by a latch spring 19 and released by one of a pair of latch release bars 16 in turn controlled by a stripper bolt 21 extending out of the base 31 so that pushing in a stripper bolt 21 pushes in a coupled latch release bar 16 which pushes two latches 17, releasing two buckles 18, each latch spring 19 pushing the latch 17 against the coupled latch release bar 16 and also against the coupled buckle 18, the interior surface 12 of the base 31 defining female threads 12 which define an axial drive screw tunnel 12a, having a male threaded drive screw 40 coupled therethrough, the screw 40 having an exterior rounded end 43 having a dowell 25, the interior end 43a of the screw 40 defining torque assembly coupling means 43a;

a clamping pad assembly 44 having a sleeve 14 defining an interior surface 14a rotatably swivelingly coupled to the rounded end 43 having a dowell 25 of the drive screw 40 and an exterior surface 33a opposite the interior surface 14a which exterior surface 33a defines a clamping pad 33 of selected size and shape, wherein the clamping pad 33 is covered by a clamping pad cover 26 of selected composition;

a clamping driver 11 having one end surface 11a shaped to removeably rotatably couple to the axial drive screw 40 torque assembly coupling means 43a, the clamping driver 11 including means to adjust said clamping driver 11 to ratchet at a selected torque;

the adjustable belt means 15 comprises two belts 15 which would, if extended, intersect at a selected angle at the base 31 and which do intersect at approximately their midpoint (not shown) 180 degrees from the base 31, and the coupling means 20 comprise D-rings 20 coupling each belt 15 and 15a to a separate buckle 18 on the base 31.

In a preferred example, the clamping driver 11 includes a spring 13 controlled ratcheting mechanism 30 controlling a ratcheting gear 36,37 which spring 13 controlled ratcheting mechanism 30 is controlled for selected torque by a set screw 24.

Prior to installation, the compress 10 is calibrated by tightening or loosening the set screw 24 which compresses or loosens a torque spring 13 which changes the pressure on the ratchet gear 36,37 until the selected ratcheting torque is obtained.

The belts 15 are then adjusted to fit the patient 10a also referred to as body 10a or body of the patient 10a.

The selected procedure is then performed on the patient 10a. After the angiogram, arteriogram or other procedure is completed, and just before the tube, other mechanism or catheter (not shown) is removed from the body 10a of the patient 10a, the belt 15 is placed around the patient 11a with the clamp 33 also called clamp pad 33 above the wound. The tube or catheter is removed while pressure is placed on the wound to stop or prevent bleeding. The clamp 33 is then tightened down by rotating the spring controlled ratcheting mechanism 30. After a selected time which may be up to ten hours or more, the wound has stopped bleeding because of clotting and the compress is removed. The patient 10a can move around during this time, a substantial improvement over the prior art where a nurse uses her hand to compress for perhaps 30 minutes, then the patient 10a lies in only one position which usually becomes cramped and uncomfortable under a sandbag for about ten hours.

A particular example of the invention has been described. Other examples will be obvious to those skilled in the art. The invention is limited only by the following claims:

I claim:

1. A mechanical compress, comprising:
   adjustable belt means;
   a base disposed around a center axis and including a clamping assembly coupled to compress means and release means;
   coupling means coupling said belt means to said clamping assembly;
   a torque adjustor coupled to said clamping assembly to adjust torque, said torque adjustor comprising ratcheting means causing said torque adjustor to ratchet when a selected torque is exceeded;
   said base has four buckles disposed to define the corners of a rectangle at the four corners of said base, each buckle being removeably coupled to said base by a different one of four swiveling spring loaded base latches, each of two pairs of latches having an end which is released by one of a pair of latch release bars in turn controlled by a stripper bolt extending out of said base so that pushing in a stripper bolt pushes in a coupled latch release bar which pushes two latches, releasing two buckles, each latch spring pushing said latch against said coupled latch release bar and also against said coupled buckle, the interior surface of said base defining female threads which define an axial drive screw tunnel, having a male threaded drive screw coupled therethrough, said screw having an exterior rounded end having a dowell, the interior end of said screw defining torque assembly coupling means;
   a clamping pad assembly having a sleeve defining an interior surface rotatably swivelingly coupled to the rounded end having a dowell of said drive screw and an exterior surface opposite said interior surface which exterior surface defines a clamping pad of selected size and shape, wherein said clamping pad is covered by a clamping pad cover of selected composition;

a clamping driver having one end surface shaped to removeably rotatably couple to said axial drive screw torque assembly coupling means, said clamping driver including means to adjust said driver to ratchet at a selected torque;

said adjustable belt means comprises two belts which would, if extended, intersect at a selected angle at said base and which do intersect at approximately their midpoint 180 degrees from said base, and said coupling means comprise D-rings coupling each belt end to a separate buckle on said base.

2. The invention of claim 1 wherein said clamping driver includes a spring controlled ratcheting mechanism controlling a ratcheting gear which spring controlled ratcheting mechanism is controlled for selected torque by a threaded set screw rotatably coupled to a torque spring via a threaded torque screw coupled through a threaded torque screw hole defined by a threaded interior surface of said clamping driver, the loosening of which set screw relieves pressure on a torque spring and the tightening of which set screw increases pressure on said torque spring, thereby changing the pressure on said ratchet gear.

* * * * *